United States Patent [19]

Mitsumata et al.

[11] Patent Number: 5,243,074
[45] Date of Patent: Sep. 7, 1993

[54] IMMUNOREAGENTS

[75] Inventors: Tadayasu Mitsumata, Hirakata, Japan; Jinsei Miyazaki, Gottingen, Fed. Rep. of Germany

[73] Assignee: Matsushita Electric Industrial Co., Ltd., Osaka, Japan

[21] Appl. No.: 616,655

[22] Filed: Nov. 21, 1990

[30] Foreign Application Priority Data

Nov. 21, 1989 [JP] Japan ............................. 1-302896
Nov. 21, 1989 [JP] Japan ............................. 1-302897

[51] Int. Cl.$^5$ .................. C07C 307/00; C07C 303/00
[52] U.S. Cl. ................................ 564/86; 436/172; 436/543; 436/544; 436/546; 436/547; 436/548; 436/815; 436/816; 436/901; 564/367; 564/370
[58] Field of Search ............ 436/546, 166, 172, 800, 436/815, 816, 901, 518, 543, 544, 547, 548; 564/86, 367, 370; 514/654

[56] References Cited

U.S. PATENT DOCUMENTS 4,161,515 7/1979 Ullman ....................... 436/800

FOREIGN PATENT DOCUMENTS 1-272967 10/1989 Japan .

OTHER PUBLICATIONS

Chemical Abstracts, vol. 89, Abstract No. 108786n, (1978).
Chemical Abstracts, vol. 106, abstract No. 207080d (1987).

*Primary Examiner*—David Saunders
*Assistant Examiner*—Christopher L. Chin
*Attorney, Agent, or Firm*—Wenderoth, Lind & Ponack

[57] ABSTRACT

An immunofluorescent assay method, characterized in using an immunodetective reagent, which is an antigen-like substance comprising a fluorescent substance and an antigen chemically bonded thereto with or without intervention of an additional chemical bond, said fluorescent substance being changed in the wavelength or intensity of the fluorescence when an antibody comes close thereto, and said antigen being specific to said antibody.

6 Claims, 4 Drawing Sheets

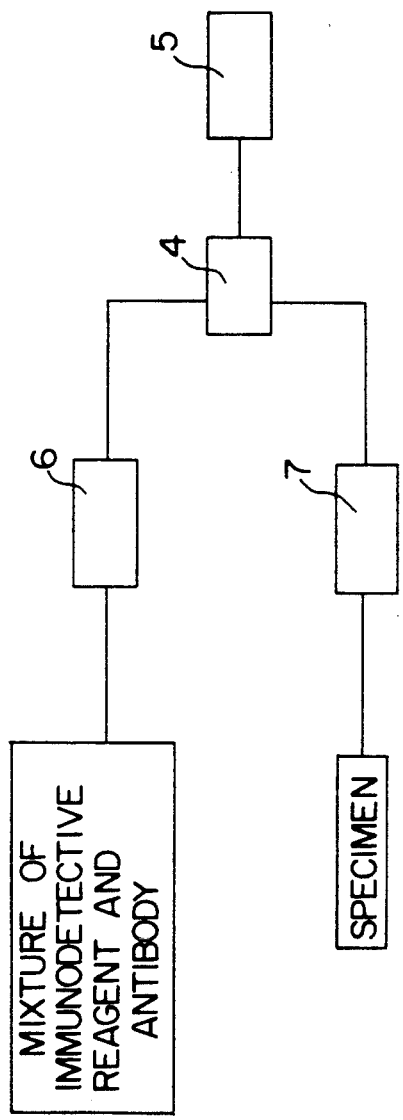
F I G. 5

IMMUNOREAGENTS

The present invention relates to immunoassay and immunoreagents. More particularly, it relates to an immunofluoroescent assay method and immunoreagents usable therein.

Immunoassay is a method for qualitative or quantitative determination of an objective substance as an antigenic substance, i.e. an antigen, in a specimen by the use of an antibody specific to said antigen. This method is characteristic in using an antibody so that qualitative or quantitative determination of an objective substance in a specimen can be surely accomplished without being prevented by any impurity in the specimen even if the content of the objective substance is very small. Accordingly, immunoassay is efficiently applicable to a specimen which contains an objective substance in such a very small amount that an analytical method using a conventional analytical apparatus or instrument (e.g. gas chromatography, liquid chromatography, mass spectrometry) can hardly detect the objective substance. For instance, immunoassay can successfully detect a certain trace antigenic component in an atmosphere or a blood.

For immunoassay, there are known a homogeneous phase method which is relatively simple in operation and accomplishes measurment in a short time but of which the sensitivity is low, and a heterogeneous phase method which is complicated in operation and takes such a long time as about 5 hours for measurement but of which the sensitivity is high.

A typical example of the homogeneous phase method is the so-called "enzyme multiplied immunoassay technique (EMIT)", in which the activity of an enzyme labeled on an antigen is decreased or increased by combination with an antibody. EMIT does not require the separation between the antibody bound to the antigen and the antibody free from the antigen (hereinafter referred to as "B/F separation") so that the operation is simple and the measurment can be accomplished within such a short period of time as about 5 to 20 minutes. However, its sensitivity is so low as about $10^{-5}$M. A typical example of the heterogeneous phase method is the so-called "enzyme-linked immunosorbent assay (ELISA)", which is advantageous in high sensitivity. Disadvantageously, however, ELISA requires the B/F separation, which includes troublesome operations. Further, the final detection in ELISA is effected by the utilization of an enzymatic reaction, which takes a considerable time.

Recently, proposal was made on an improved immunoassay method which has simplicity in operation like a homogeneous phase method and high sensitivity like a heterogeneous phase method (Japanese Patent Application Nos. 75447/88 and 184951/88). In this method, measurement is speeded up by the utilization of a phenomenon that the fluorescence of an antibody produced around 320 nm by irradiation of an exciting line of about 280 nm changes on the combination of the antibody with an antigen. However, the wavelength of the exciting line is close to that of the produced fluorescence so that the Raman scattering of water may produce noise. Also, the exciting line and the produced fluorescence are short in wavelength so that the fluorescence produced by naturally existing proteins or organic substances may be detected as noise.

As the result of an extensive study to overcome the above drawbacks and problems as seen in the known immunoassay methods, there is now proposed a immunofluorescent assay method, which is characteristic in using an immunodetective reagent, which is an antigen-like substance comprising a fluorescent substance and an antigen chemically bonded thereto with or without intervention of an additional chemical linkage, said fluorescent substance being changed in the wavelength or intensity of the fluorescence when an antibody comes close thereto, and said antigen being specific to said antibody.

Explaining the principle on which the immunofluorescent assay method of the invention is based, the antigen-binding site in an antibody shows hydrophobic property due to the influence of the environment surrounding said site. Because of this reason, a free antigen present and an antibody-bound antigen in a hydrophilic medium differ in their surrounding environments so that the fluorescent substance in the immunodetective reagent of the invention gives different intensities of fluorescence. By the utilization of such difference in fluorescence intensity, detection of an objective substance as an antigen is made possible.

Further, a proper selection of the fluorescent substance in the immunodetective reagent of the invention makes the wavelengths of the exciting line and the produced fluorescence longer than those of the proteins as impurities. As the result, it becomes possible to detect the objective substance in a specimen even if the specimen is contaminated with proteinous impurities. Likewise, the noice which may be caused by Raman scattering due to water may be prevented.

Accordingly, the immunofluorescent assay method of the invention can advantageously accomplish measurement of an objective substance, even when present in a trace amount in a specimen, with high sensitivity by simple operation within a short period of time. Even when a specimen is contaminated with proteins or contains water, measurement can be made without the noise, which may be caused by such proteins or water.

As stated above, the most characteristic feature of the immunofluorescent assay method according to the invention resides in the use of a certain specific immunodetective reagent. Namely, the immunodetective reagent is an antigen-like substance which comprises an antigen and a fluoroescent substance chemically bound thereto with or without intervention of an additional chemical linkage. The chemical linkage is helpful for making the chemcical binding easier. Chemical binding may be effected by a per se conventional procedure such as the reaction of an antigen or its reactive derivative with a fluorescent substance or its reactive derivative.

The antigen or its reactive derivative used for preparation of the immunodetective reagent may be an objective substance to be detected or its chemical analogue, or their reactive derivatives. The scope of the chemical analogue may be the one covering any substance having the same fundamental chemical structure as the objective substance to be detected but being modified to such an extent that it is immunologically sensitive to the antibody specific to said objective substance. The objective substance to be detected may be chosen from pharmaceuticals, agro-chemicals, explosives, pollution materials, etc. Typical examples of the objective substance are methamphetamine, amphetamine, ephedrine, etc., and their detection from specimens such as human urine can be easily accomplished by this invention.

As the fluorescent substance usable in the immunodetective reagent, there are exemplified dansyl chloride, fluorescamine, o-phthalaldehyde, fluorescein isothiocyanate, acridine orange, 9-aminoacridine, acrinamine, etc. Among them, the use of such a fluorescent substance which can utilize an exciting line of long wavelength to produce long wavelength fluorescence as dansyl chloride (producing fluorescence of 510 nm) is favorable, because the noise fluorescence due to proteinous impurities or water in the specimen can be avoided.

Explaining the present invention more in details taking detection of methamphetamine, amphetamine or ephedrine as an example, the favorable antigen-like substance for the above purpose is representable by the formula:

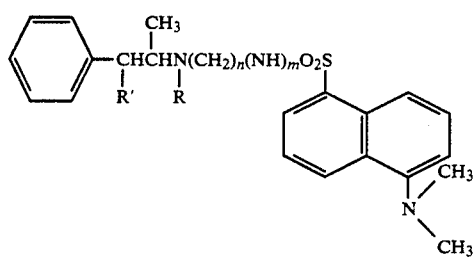

wherein R is hydrogen or methyl, R' is hydrogen or hydroxyl, m is an integer of 0 or 1 and n is an integer of 0 to 10, preferably of 0 to 6, provided that (1) when m is 0, n is 0 and (2) when m is 1, n is not 0. When n is more than 10, any significant difference in fluorescence intensity will be not produced between the immunodetective substance free from the antibody and the immunodetective substance bound to the antibody and not usable in this invention. Preferred are the compounds of the formula (I) wherein R' is hydrogen, which are suitable for detection of methamphetamine or amphetamine. Particularly preferred are the compounds of the formula (I) wherein R is hydrogen or methyl, R' is hydrogen, m is 1 and n is 4, because they can be readily produced using the easily available starting materials and, in addition, the binding property between the antibody and the immunodetective reagent and the binding property between the antibody and the objective substance (i.e. antigen) are well balanced. Also, the compounds of the formula (I) wherein R is hydrogen or methyl, R' is hydrogen, m is 0 and n is 0 are favorable, because they can be produced by a simple procedure and are significant in the variation of the fluorescence intensity between the immunodetective reagent free from the antibody and the immunodetective reagent bound to the antibody even when the extent of the hydrophobic property surrounding the antigen-binding site in the antibody is low.

The immunofluorescent assay method of the invention is normally carried out in an aqueous medium, preferably with appropriately controlled pH. Thus, phosphate-buffered physiologically saline solution is one of the most preferred medium in which the immunoflorescent assay method is performed.

On the actual use, the immunodetective reagent is employed in the form of aqueous solution, preferably controlled at pH with phosphate buffer. For the convenience on storage or transportation, it is commercially supplied in a solid form, for instance, as a lyophilized product of its aqueous solution. The antibody and the specimen are also favorably employed in aqueous solutions, preferably controlled at pH with phosphate buffer, for the practical use. When desired, the immunodetective reagent and the antibody may be mixed together previously or supplied in a mixture form as an aqueous solution or its lyophilized product.

When, for instance, the objective substance (i.e. antigen) is methamphetamine and the fluorescent substance is a dansyl group, the immunofluoroescent assay method may be carried out as follows:

Methamphetamine as the antigen and a dansyl group as the fluorescent substance are chemically bound together, optionally with intervention of any chemical linkage such as an alkylamine linkage to give an antigen-like substance, which is useful as an immunodetective reagent. The immunodetective reagnet is admixed with an antibody specific to methamphetamine as the antigen, usually in an aqueous medium, whereby the antibody is bound to the immunodetective reagent and the fluorescence intensity of the fluoroescent substance in the immunodetective reagent is increased.

Then, a specimen which may contain methamphetamine as the objective substance to be detected is added thereto.

When the specimen contains methamphetamine, this substance is bound to the antibody, and the binding between the antibody and the immunodetective reagent is broken, whereby the fluorescence of the immunodetective reagent is decreased.

Therefore, measurement of the fluorescence of a mixture of the specimen with the immunodetective reagent makes it possible to determine whether methamphetamine is present in the specimen. It is also possible to determine quantitatively methamphetamine in the specimen by the previously establishment of the relationship between the amount of methamphetamine and the decrease of the fluorescence intensity.

In the above procedure, the reaction always proceeds in a homogeneous phase (liquid phase), and no enzymatic reaction is utilized. Thus, the time for measurement can be much shortened. Further, a dansyl group can produce a significant difference between the wavelength of the exciting line and the wavelength of the produced fluorescence so that the influence by the Raman scattering is easily avoided. The wavelengths of the exciting line and the produced fluorescence are much longer than those of proteins, and the influence by the proteinous impurities can be also avoided.

Practical and presently preferred embodiments of the invention are illustratively shown in the following Examples wherein the abbreviations have the following meanings: MW, molecular weight; TLC, thin layer chromatography; PBS, phosphate-buffered physiological saline; DNSCl, dansyl chloride; MA, methamphetamine; ABMA, N-(4-aminobutyl)methamphetamine; DNSABMA, N-(4-dansylaminobutyl)methamphetamine; DNSMA, N-dansylmethamphetamine; AP, amphetamine; ABAP, N-(4-aminobutyl)amphetamine; DNSABAP, N-(4-dansylaminobutyl)amphetamine; DNSAP, N-dansylamphetamine.

FIG. 5 depicts another embodiment of an automatic device for carrying out a fluorescence measurement according to the invention.

EXAMPLE 1

Figure 1:
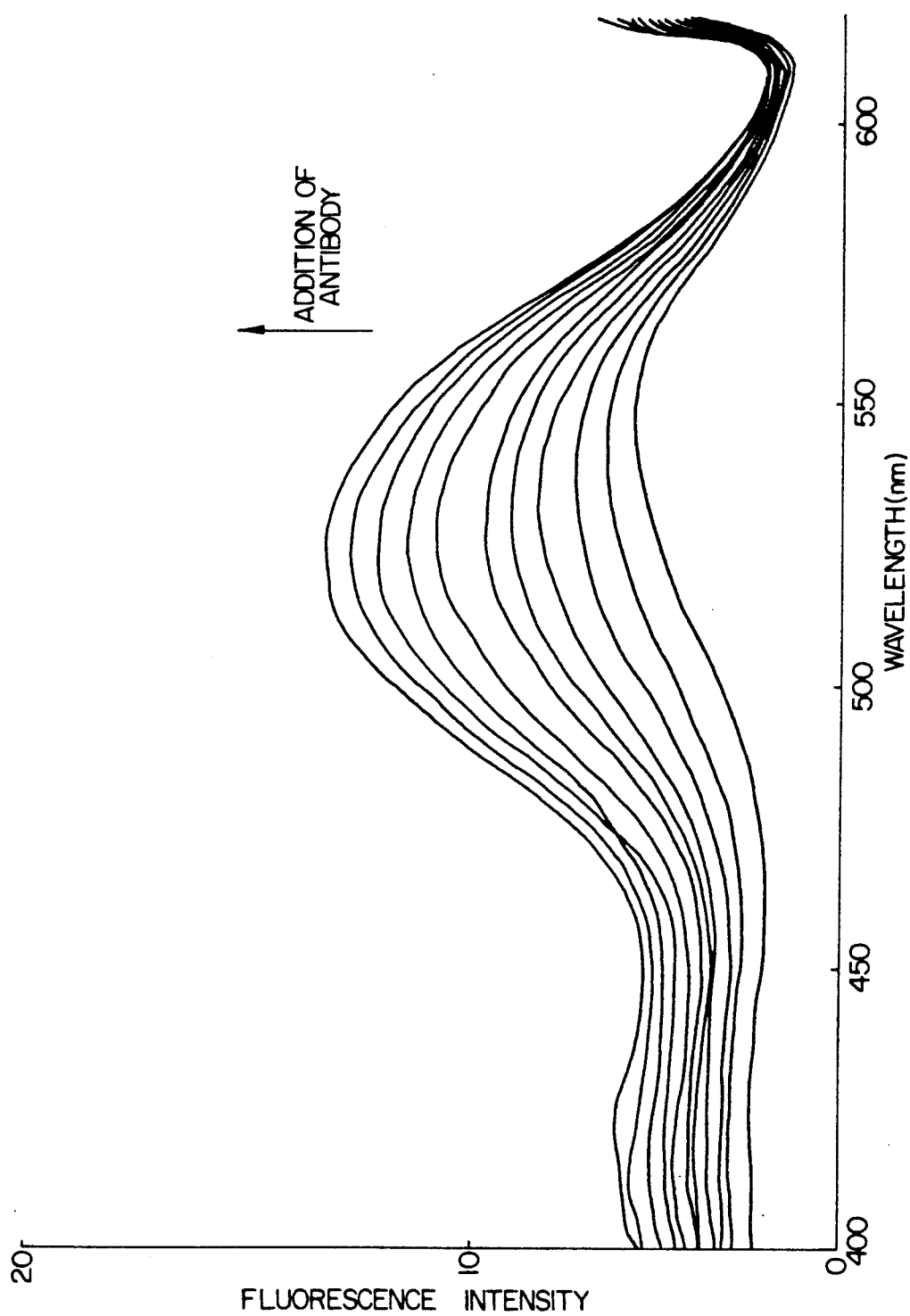
FIG. 1 is a graph of fluorescence intensity as a function of wavelength wavelength upon addition of antibodies in accordance with the invention.

Dansyl chloride (MW=269.75, 232.2 mg, 0.861 mmol) was dissolved into acetone (6 ml), and the resultant solution was added to N-(4-aminobutyl)methamphetamine (MW=220.6, 154.7 mg, 0.702 mmol). After addition of anhydrous potassium carbonate (MW=138.21, 242.8 mg, 1.757 mmol) ground in a mortar thereto, the resultant mixture was stirred at room temperature (about 25° C.) for 7.5 hours. The progress of the reaction was monitored with TLC under the following conditions:

TLC: silica gel 60 (Merck, Art.5549, 50×75×0.2 mm);
Eluent: acetone;
Rf: DNSCl: 0.72–0.66; DNSABMA: 0.45–0.17; ABMA: –0.

Detection of dansyl chloride and N-(4-dansylaminobutyl)methamphetamine was carried out by irradiation of ultraviolet rays at 366 nm to produce light green fluorescence. Detection of N-(4-aminobutyl)methamphetamine was effected by irradiation of ultraviolet rays at 254 nm to cause slight absorption of ultraviolet rays and also by ninhydrin reaction.

After confirmation of the consumption of N-(4-aminobutyl)methamphetamine, the reaction mixture was filtered to remove potassium carbonate, and the filtrate was distilled to remove acetone, whereby a yellow liquid (297.4 mg) was obtained. The yellow liquid was dissolved in acetone (2 ml), charged onto three thin layers (Merck, Art.5717, 200×200×2 mm) and developed with acetone. The portion corresponding to N-(4-dansylaminobutyl)methamphetamine was scraped off and extracted with methanol. Evaporation of the solvent from the methanol extract gave N-(4-dansylaminobutyl)methamphetamine (MW=453.65, 140 mg, 0.309 mmol) as a pale yellow liquid. Yield, 44.0%.

The reaction in the above production is representable by the following formulas:

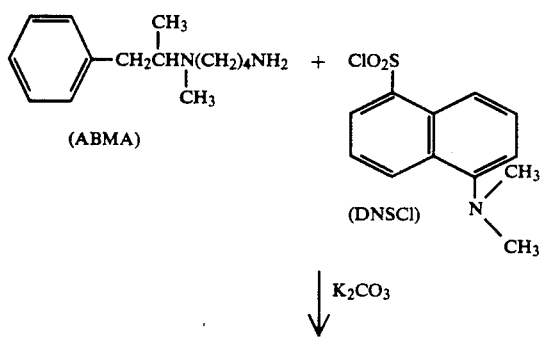

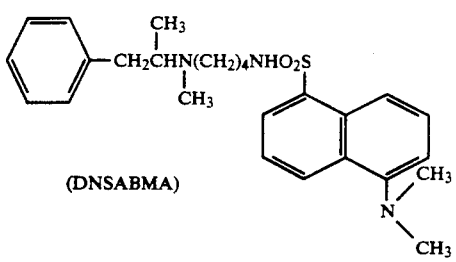

To 2.5 ml of a PBS solution of N-(4-dansylaminobutyl)methamphetamine ($10^{-7}$M), 20 or 40 μl of a PBS solution of a monoclonal antibdy (IgG) ($2.5 \times 10^{-8}$M) was added, and the resultant mixture was stirred with a Pasteur pipette and subjected to measurment of fluorescence under the following conditions:

Exciting line wavelength: 528 nm;
Band pass: exciting side, 20 nm; fluoresced side, 10 nm;
Scanning speed: 120 nm/min;
Fluorescene wavelength: 400–620 nm;
Intensity range: 0–20.

Still, the PBS solution of N-(4-dansylaminobutyl)methamphetamine as above used was prepared by dissolving N-(4-dansylaminobutyl)methamphetamine in PBS to make a concentration of $10^{-7}$M, followed by filtration with a filter of 0.45 μm. The monoclonal antibody (IgG) having a binding constant of $10^{-7}$ to methamphethamine was prepared by a per se conventional manner, and the PBS solution of a monoclonal antibody was prepared by subjecting a PBS solution of said IgG to filtration with a filter of 0.45 μm; its absorption intensity at 280 nm was 0.563; when $A_{280}$ of 1% IgG is 15, the IgG concentration was $2.5 \times 10^{-6}$M.

The results of the measurement are shown in FIG. 1 of the accompanying drawings, from which it is understood that the fluorescence intensity of N-(4-dansylaminobutyl)methamphetamine increased with the addition of the antibody. Simultaneously, the maximum fluorescence wavelength initially at 550 nm was transferred to 523 nm. Such phenomenon is frequently observed when the polarity around a fluorescnt substance is lowered. Therefore, the above transfer might be explained as follows: the methamphetamine portion in N-(4-dansylaminobutyl)methamphetamine was combined to the antibody, and the dansyl portion came close to the antibody so that the polarity was lowered in comparison with that in a free state.

On the basis of the above results, the detection of methamphetamine through the inhibitory effect of methamphetamine on the binding of N-(4-dansylaminobutyl)methamphetamine to the antibody was examined.

Namely, a PBS solution of N-(4-dansylaminobutyl)methamphetamine ($1.0 \times 10^{-7}$M, 546 μl), a monoclonal antibody (IgG) solution (24 μl) and a methamphetamine solution having a designed concentration (30 μl) were charged in a quartz-made microcell, and the resultant mixture was stirred for 30 seconds and then subjected to measurement of fluorescence intensity under the following conditions:

Exciting line wavelength: 328 nm;
Band pass: exciting side, 20 nm; fluoresced side, 20 nm;
Measurement wavelength: 530 nm.

Still, the PBS solution of N-(4-dansylaminobutyl)methamphetamine as above used was prepared by dissolving N-(4-dansylaminobutyl)methamphetamine in PBS to make a concentration of $10^{-7}$M, followed by filtration with a filter of 0.45 μm. The monoclonal antibody solution was prepared by subjecting a PBS solution of the IgG described above to filtration with a filter of 0.45 μm; its absorption intensity at 280 nm was 0.563; when $A_{280}$ of 1% IgG is 15, the IgG concentration was $2.5 \times 10^{-6}$M.

On measurement of the fluorescence intensity, the average of the measured values for 5 seconds was obtained, and measurement was made two times for each test sample. The results are shown in FIG. 2, which is a graph obtained by plotting the measured fluorescence intensity for the methamphetamine concentration.

Figure 2:
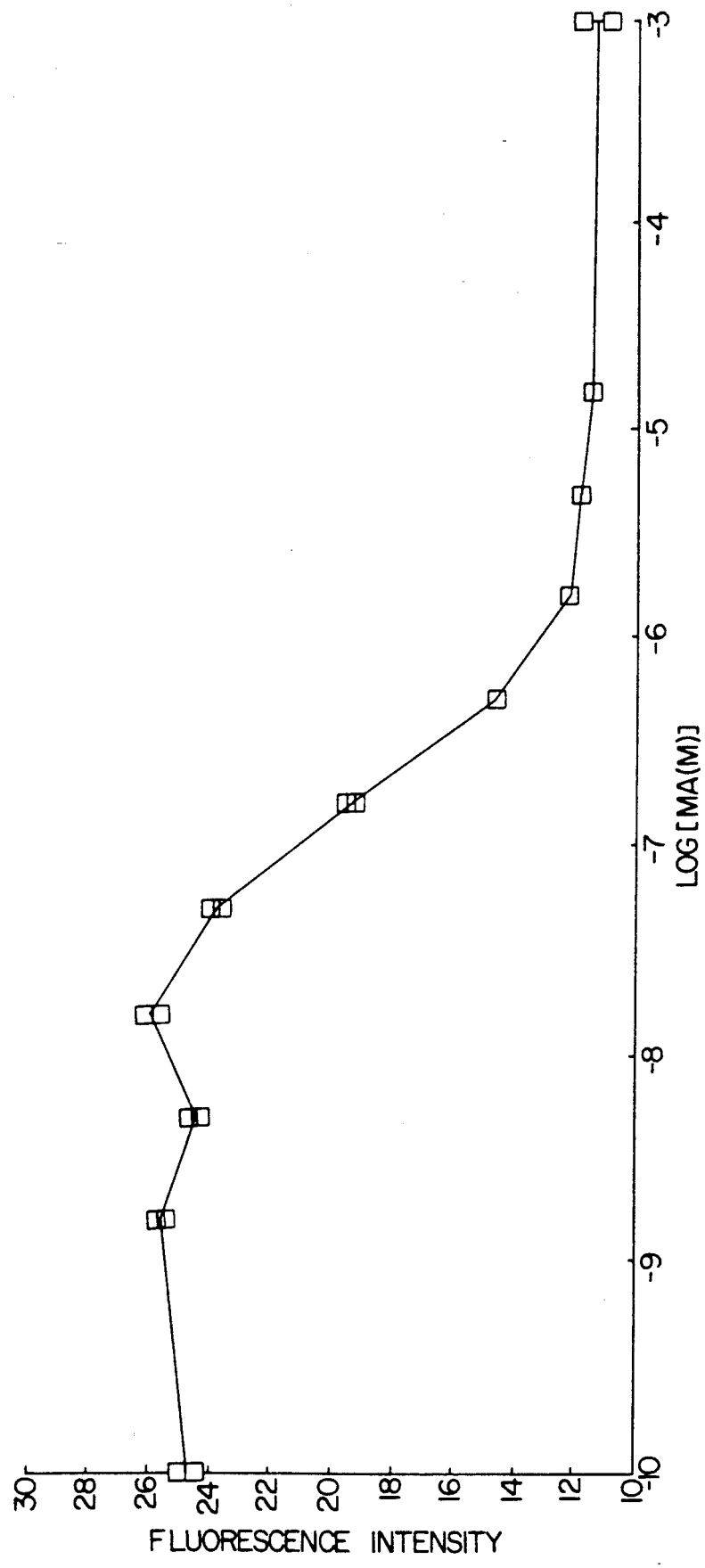
FIG. 2 is a graph of fluorescence intensity as a function of methamphetamine concentration in accordance with the invention.

In FIG. 2, the methamphetamine concentration giving 50% change is about $10^{-6.7}$M. The sensitivity resulting from this value is nearly equal to that of ELISA carried out under the same conditions as above. On the other hand, the time required for the reaction in the above method was only about 30 seconds, which were taken for addition of the methamphetamine solution and stirring.

Accordingly, it may be said that the immunofluorescent assay method of the invention can achieve measurement rapidly without lowering the sensitivity. Since the the exciting line and the produced fluorescence have a difference of 200 nm in wavelength, Raman scattering (about 360 nm) does not produce any influence. Further, the exciting line (328 nm) and the produced fluorescence (530 nm) have longer wavelengths than those of the contaminating protein (exciting line, 280 nm; produced fluorescence, 320 nm), the influence by the contaminating protein can be readily avoided.

EXAMPLE 2

In the same manner as in Example 1 but using methamphetamine in place of N-(4-aminobutyl)methamphetamine, there was produced N-dansylmethamphetamine of the formula:

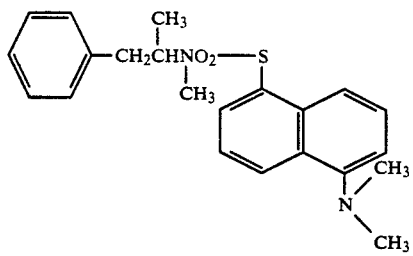

Using the above obtained N-dansylmethamphetamine, detection of methamphetamine was carried out in the same manner as in Example 1. The results are shown below.

Optimum excitng line wavelength: 328 nm;
Maximum fluorescence wavelength: 550 nm (antibody not added); 530 nm (antibody added);
Methamphetamine concentration on 50% change in fluorescence: $10^{-8.5}$M The immunodetective reagent of this Example 2 is thus effective for detection of methamphetamine.

EXAMPLE 3

In the same manner as in Example 1 but using N-(4-aminobutyl)amphetamine in place of N-(4-aminobutyl)methamphetamine, there was produced N-(4-dansylaminobutyl)amphetamine of the formula:

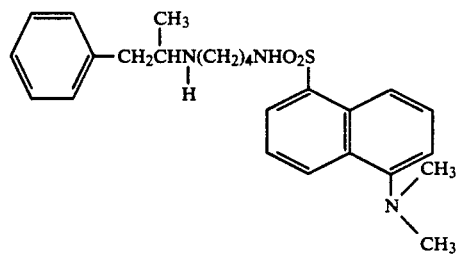

Using the above obtained N-(4-dansylaminobutyl)amphetamine, detection of methamphetamine was carried out in the same manner as in Example 1. The results are shown below.

Optimum exciting line wavelength: 328 nm;
Maximum fluorescence wavelength: 550 nm (antibody not added); 530 nm (antibody added);
Methamphetamine concentration on 50% change in fluorescence: $10^{-7.2}$M.

The immunodetective reagent of this Example 3 is thus effective for detection of methamphetamine.

EXAMPLE 4

In the same manner as in Example 1 but using amphetamine in place of N-(4-aminobutyl)methamphetamine, there was produced N-dansylamphetamine of the formula:

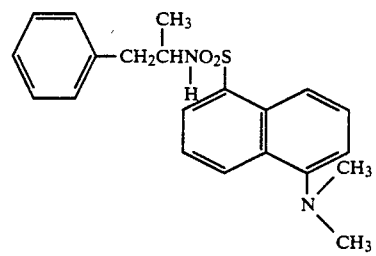

Using the above obtained N-dansylamphetamine, detection of methamphetamine was carried out in the same manner as in Example 1. The results are shown below.

Optimum excitng line wavelength: 328 nm;
Maximum fluorescence wavelength: 550 nm (antibody not added); 530 nm (antibody added);
Methamphetamine concentration on 50% change in fluorescence: $10^{-7.0}$M.

The immunodetective reagent of this Example 4 is thus effective for detection of methamphetamine.

For carrying out the immunofluoroescent assay method of the invention, it is convenient to prepare previously a mixture of the immunodetective reagent and the antibody. Further, one or more (preferably all) of the reagents may be formulated, for instance, in a PBS solution of around pH 6.5 to 7.5 so that the reproducibility of the test method and the storage stability of the antibody are enhanced. Furthermore, the storage stability of the antibody will be more enhanced by lyophilizing a mixture of the antibody and the immunodetective reagent, usually, in a PBS solution and storing the lyophilized product.

EXAMPLE 5

Figure 3:
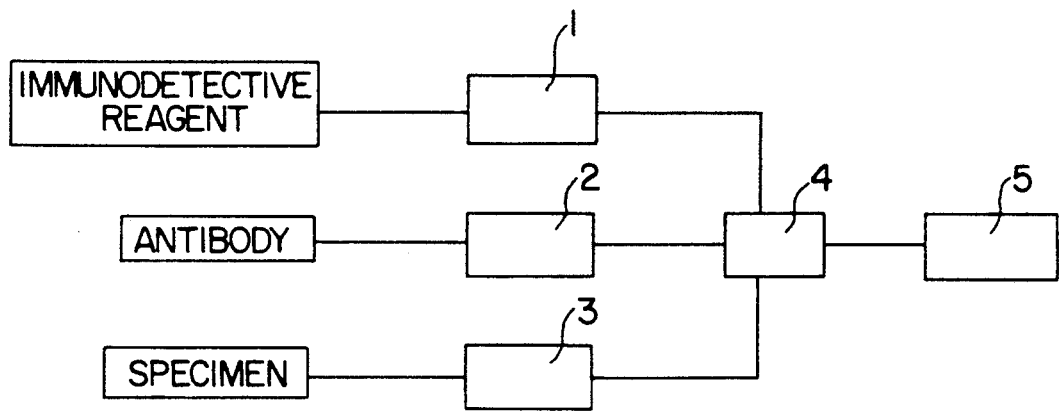
FIG. 3 depicts an automatic device for carrying out a fluorescence measurement according to the invention.

A typical example of the contruction of an automatic device for carrying out measurment according to the invention is shown in FIG. 3 wherein 1, 2 and 3 are quantitative feeding pumps, which are respectively connected to a container for the immunodetective reagent solution (concentration, $10^{-7}$M), a container for the antibody solution (concentration, $10^{-7}$M) and a container for the specimen solution. 4 is a mixing apparatus provided with valves, which open or close the passages from the containers to a fluorescent intensity detector 5 having a flow cell, for instance, of 10 $\mu$l in capacity and monitoring continuously a fluorescence intensity at 530 nm produced by an exciting line of 328 nm.

With the start of the measurement, the pumps 1, 2 and 3 are operated to send 50 $\mu$l of each of the three solutions to the mixing apparatus 4. After mixing well, the mixture is sent to the detector 5. In the detector 5, air or pure water flows so that no fluorescence is usually produced, but when the mixture is sent thereto, the production of fluorescence is caused by the immunodetective reagent. The intensity of this fluorescence is decreased in the presence of an objective substance to be detected such as methamphetamine according to the principle as shown in Example 1. The presence or absence of the objective substance in a specimen can be thus determined on the decrease of the fluorescence intensity, i.e. the height of the fluorescent peak.

Figure 4:
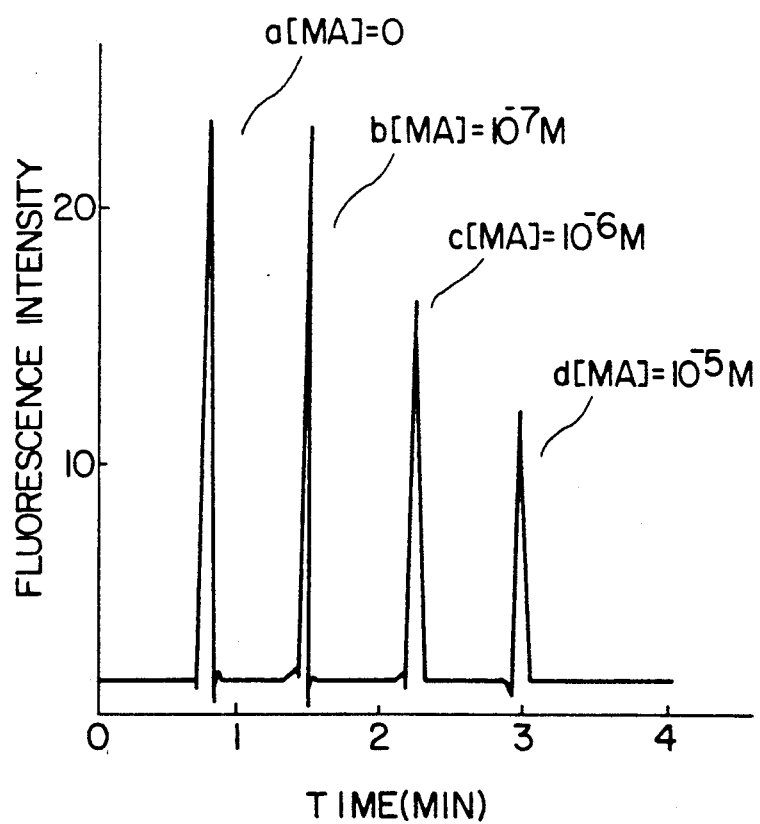
FIG. 4 is a graph depicting change in fluorescence intensity with respect to time using the device shown in FIG. 3.

Automatic measurement of methamphetamine was carried out by the use of the device as shown in FIG. 3, and the results are shown in FIG. 4 wherein the ordinate indicates a fluorescence intensity and the abscissa indicates a time (minute). The curves a, b, c and d are respectively concerned with pure water not containing methamphetamine, a specimen containing methamphetamine in a concentration of $10^{-7}$M, a specimen containing methamphetamine in a concentration of $10^{-6}$M and a specimen containing methamphetamine in a concentration of $10^{-5}$M. As understood from FIG. 4, methamphetamine can be measured at a sensitivity of $10^{-6}$ within one minute by the use of said device.

EXAMPLE 6

Instead of an automatic device having three pumps corresponding to each of the three solutions, i.e. the immunodetective reagent solution, the antibody solution and the specimen solution, as shown in Example 5 (FIG. 3), this Example gives an automatic device having two pumps corresponding to each of the two solutions, i.e. the mixture solution comprising an immunodetective reagent and an antibody and the specimen solution, as shown in FIG. 5. In this Figure, 6 and 7 are quantitative feeding pumps, of which the pump 6 sends the mixture solution to a mixing apparatus 4 and the pump 7 sends the specimen solution to said mixing apparatus. 5 is a fluorescent intensity detector.

In the same manner as in Example 5, the automatic device is operated to accomplish measurement of an objective substance to be detected at the same sensitivity as in Example 5. The automatic device of this Example is more simpler than that of Example 5 and hence more preferable.

The above mentioned Examples illustrate the detection and measurement of pharmaceuticals such as amphetamine. In the same manner, the immunofluorescent assay method of this invention can accomplish the detection or measurement of trace materials in various fields, including pathogens or disease markers in the field of clinical examination.

What is claimed is:

1. An immunodetective reagent consisting essentially of N-(4-dansylaminobutyl)amphetamine.

2. An immunodetective reagent consisting essentially of N-(4-dansylaminobutyl)methamphetamine.

3. An immunoreagent system which comprises N-(4-dansylaminobutyl)amphetamine and an antibody specific to amphetamine.

4. An immunoreagent system which comprises N-(4-dansylaminobutyl)methamphetamine and an antibody specific to methamphetamine.

5. The immunoreagent system according to claim 3, which further comprises a buffering agent.

6. The immunoreagent system according to claim 4, which further comprises a buffering agent.

* * * * *